United States Patent [19]

Masini

[11] Patent Number: 5,571,203
[45] Date of Patent: Nov. 5, 1996

[54] BONE-CONSERVING HIP SYSTEM

[76] Inventor: Michael A. Masini, 4817 Hillway Ct., Ann Arbor, Mich. 48105

[21] Appl. No.: 373,174

[22] Filed: Jan. 17, 1995

Related U.S. Application Data

[63] Continuation-in-part of Ser. No. 79,366, Jun. 18, 1993, abandoned.

[51] Int. Cl.$^6$ .................................................. A61F 2/36
[52] U.S. Cl. ............................................................ 623/23
[58] Field of Search .................................. 623/16, 18, 22, 623/23

[56] References Cited

U.S. PATENT DOCUMENTS

| | | | |
|---|---|---|---|
| 3,064,645 | 11/1962 | Ficat et al. | 623/23 |
| 3,781,917 | 1/1974 | Mathys | 623/23 |
| 4,129,903 | 12/1978 | Huggler. | |
| 4,608,053 | 8/1986 | Keller | 623/23 |
| 4,795,473 | 1/1989 | Grimes | 623/23 |
| 4,976,740 | 12/1990 | Kleiner | 623/23 |
| 5,167,666 | 12/1992 | Mattheck et al. | 623/23 |
| 5,181,928 | 1/1993 | Bolesky et al. | 623/23 |

FOREIGN PATENT DOCUMENTS

| | | |
|---|---|---|
| 2651118 | 3/1991 | France. |
| WO9118559 | 12/1991 | WIPO. |

*Primary Examiner*—Mary Beth Jones
*Attorney, Agent, or Firm*—Gifford, Krass, Groh, Sprinkle, Patmore, Anderson & Citkowski

[57] ABSTRACT

In a bone-conserving hip system, the proximal end of the femur is resected to accept a body with a flat mating surface. An anchoring rod extends from a rim on the body through a hole bored through the femoral shaft and is secured to the lateral side of the femur, thereby converting tensile stress introduced at the ball end of the head/neck assembly into compressive forces directed along the longitudinal axis of the femur. Anti-rotation means, preferably in the form of a plurality of fins extending radially outward from the housing, are used minimize rotation relative to the femur once the prosthesis is seated.

17 Claims, 5 Drawing Sheets

BONE-CONSERVING HIP SYSTEM

REFERENCE TO RELATED APPLICATIONS

This is a continuation-in-part of U.S. patent application Ser. No. 08/079,366, filed Jun. 18, 1993, now abandoned.

FIELD OF THE INVENTION

This invention relates generally to femoral prosthetic devices and, in particular, to a hip system that manages stress and preserves bone as a host bed for revision, if required.

BACKGROUND OF THE INVENTION

In the past, surface replacement of the acetabulum or "socket" portion of a hip prosthesis was used as a form of conservative arthroplasty in the hope of preserving femoral bone stock. This approach has essentially been abandoned, however, due to a high rate of acetabular failure resulting from several factors. For one, the large head of the femur associated with resurfacing leads to the acetabula being exposed to a large frictional torque. Secondly, acetabular implants must be thin in order to accommodate the large femoral head, and early clinical failure resulted due to mechanical loosening and volumetric wear.

In concert with bone conservation, attention to stress distribution within the femur after implantation of a prosthesis has become increasingly important, as it is now recognized that excess stresses induced by the implant may lead to further deterioration and necrosis. For example, conventional intramedullary implants, those secured in the marrow canal of the femur, may result in serious complications, in some cases only a few years after implantation, due to the unmanaged rotational and tensional forces transferred to the implant area. This situation presents a serious lack of alternatives, especially for the younger patient, as each arthroplasty procedure consumes additional bone material, thereby rendering each successive corrective surgery increasingly radical.

Such problems have led to the exploration of so-called "extramedullary" prosthetic joints such as that disclosed in U.S. Pat. No. 4,129,903 (Huggler) and in U.S. Pat. No. 4,795,473 (Grimes) both of which are incorporated herein by reference. In these approaches, the femoral shaft is cut to provide a flat surface against which a thrust plate is positioned, the plate being anchored by a tie rod extending through the proximal end of the femur and secured at a point along the lateral shaft. In both these approaches, however, the femoral cut is made at an acute angle relative to the longitudinal axis of the femoral shaft, resulting in residual play of the implant and the tie rod as the patient's weight bears down on the prosthesis during exercise of the joint. As such, forces remain which limit the lifetime of such implants.

Thus, there remains an unsatisfied need for a hip system which conserves both femoral and acetabular bone material while, at the same time, manages stresses induced through the implant, thereby reserving sufficient material to provide a host bed for primary hip arthroplasty, if subsequently required. Such a system should be particularly valuable for the younger patient.

SUMMARY OF THE INVENTION

Accordingly, the present invention is directed toward a hip system which conserves bone material upon installation, and which restricts the motion of the implant during use so as to minimize further deterioration. The system makes use of a flanged body having a bottom surface adapted to mate against the corresponding surface resected on the proximal end of the femoral shaft. In the preferred embodiment, this resection is substantially transverse to the longitudinal axis of the femur. A rod, adapted to extend downwardly and through the shaft of the femur has an upper end secured at a point proximate to the periphery of the flange, and a second end which anchors to the lateral outer cortex of the shaft, thereby establishing a pivot point where the rod engages with the flange. A bent neck component extends upwardly from the flanged body and terminates in a ball-shaped head unit adapted for acetabular engagement. Owing to the pivoting action made possible by the anchoring rod, forces applied to the head portion during use are converted into compressive stress directed substantially along the longitudinal axis of the femur through the interface between the bottom surface of the flange and resected surface. In the preferred embodiments, the resection is made substantially transverse to the femoral axis, and anti-rotation means are included which extend downwardly from the bottom surface of the flange, but with the downward extent being preferably contained within the metaphyseal region of the bone.

In alternative embodiments of the invention, separate head/neck and ball components are used to provide flexibility in configuring the hip system to a particular patient prior to the formation of a final, unitary structure. For example, in one embodiment, the system uses a separate head/neck component which attaches to the flanged body using a self-holding type of taper, preferably of the Morse type. In an alternative embodiment, the neck is integrally formed on the upper portion of the flanged body, and a separate ball component is provided which attaches to an exposed stem end on the neck, again making use of a self-holding type of tapering, preferably Morse. In a further alternative embodiment, both the connection points between a neck component and the flanged body and that between the neck component and a ball component connected through such self-holding taper connection systems.

The present invention also includes a novel method of installing the hip system, including the method by which the femoral shaft is cut at its proximal end. A passage is bored through the shaft, the anchoring rod is introduced into the passage, and the head/neck and/or ball components are tested to determine an optimal physical match to the patient's skeletal structure after the main body is mounted and secured. The separable components, flanged body, and anchoring rod system can be made from any orthopedic materials, including titanium and metal alloys, and the prothesis-bone interfaces may be cemented or adapted to encourage porous ingrowth.

DETAILED DESCRIPTION OF THE PREFERRED EMBODIMENTS

Figure 1:
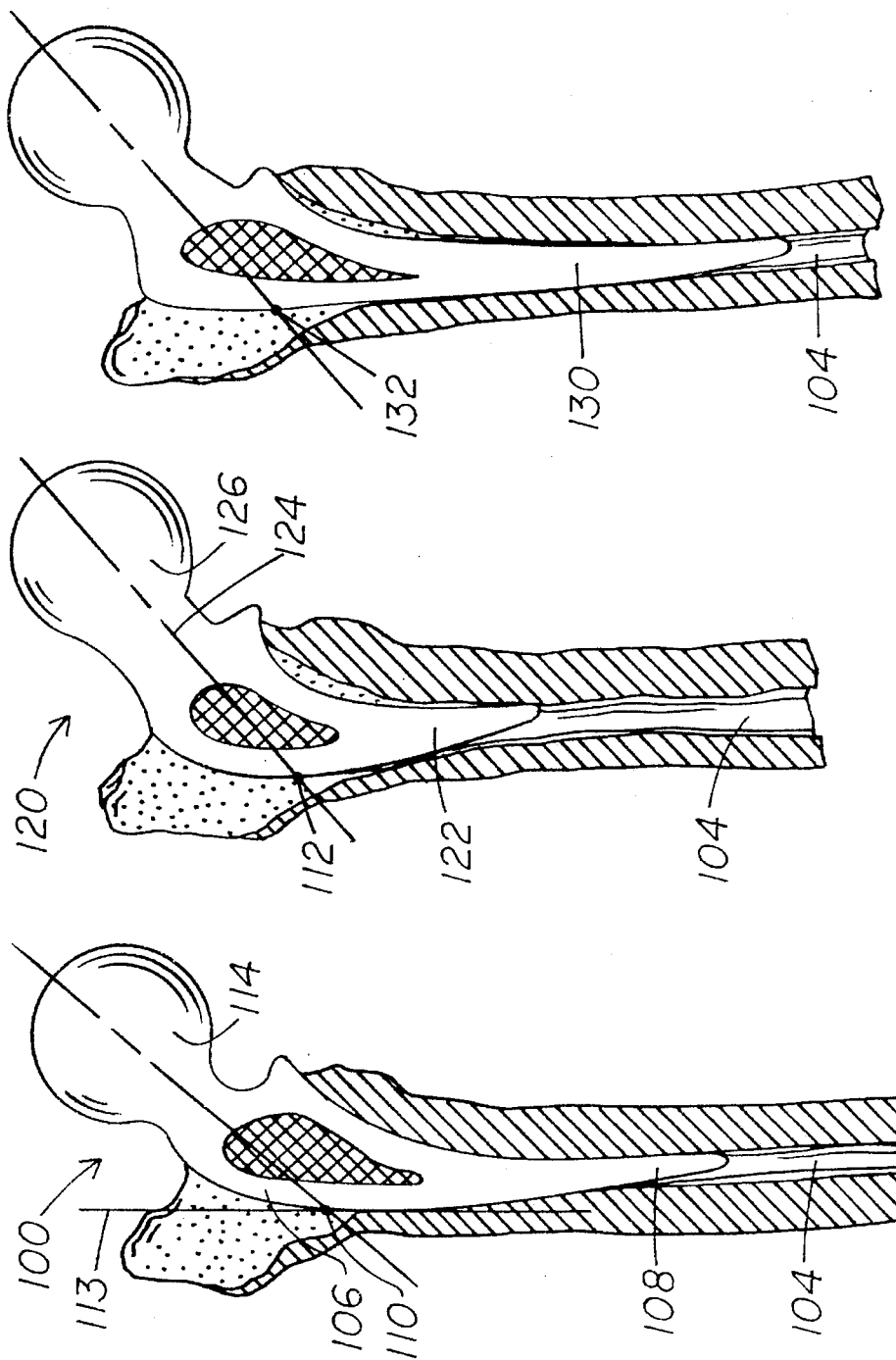
FIG. 1A is a side-view drawing in partial cross-section of a first type of prior-art intramedullary implant.
FIG. 1B is a side-view drawing in partial cross-section of a second type of prior-art intramedullary implant.
FIG. 1C is a side-view drawing in partial cross-section of a third type of prior-art intramedullary implant.

In FIG. 1 there are shown three typical prior-art intramedullary implants with cortical bone removed to illustrate how they are seated within the medullary cavity or canal 104 of the femur. FIG. 1A, shown generally at 100, illustrates one popular intramedullary configuration, that in which a shank portion 106 curves gradually as it extends into the canal, becoming nearly straight at its lower tip 108. Assuming the stem is firmly cemented in place, the area of maximum tensile stress on the stem is that area at or near the point 110 where a line 112 drawing through the center of the head 114 intersects with a line 113 along the lateral aspect of the stem. (See Campbell's Orthopedics, Sixth Edition, incorporated herein by reference, at p. 2184, which concerns arthroplasty.)

FIG. 1B shows at 120 a different prior-art intramedullary implant exhibiting a stem 122 exhibiting a more pronounced curvature. In this instance, a line 124 drawn through the center of the head 126 intersects at point 112, and the interface proximate to the implanted stem may be subjected to even greater tensile stress than the case illustrated in FIG. 1A. If the stem is more or less straight, such as stem 130 in FIG. 1C, the area of maximum tensile stress may be dictated by the point 132 where the stem is widest, in contrast with the curved designs of FIGS. 1A and 1B.

Figure 2:
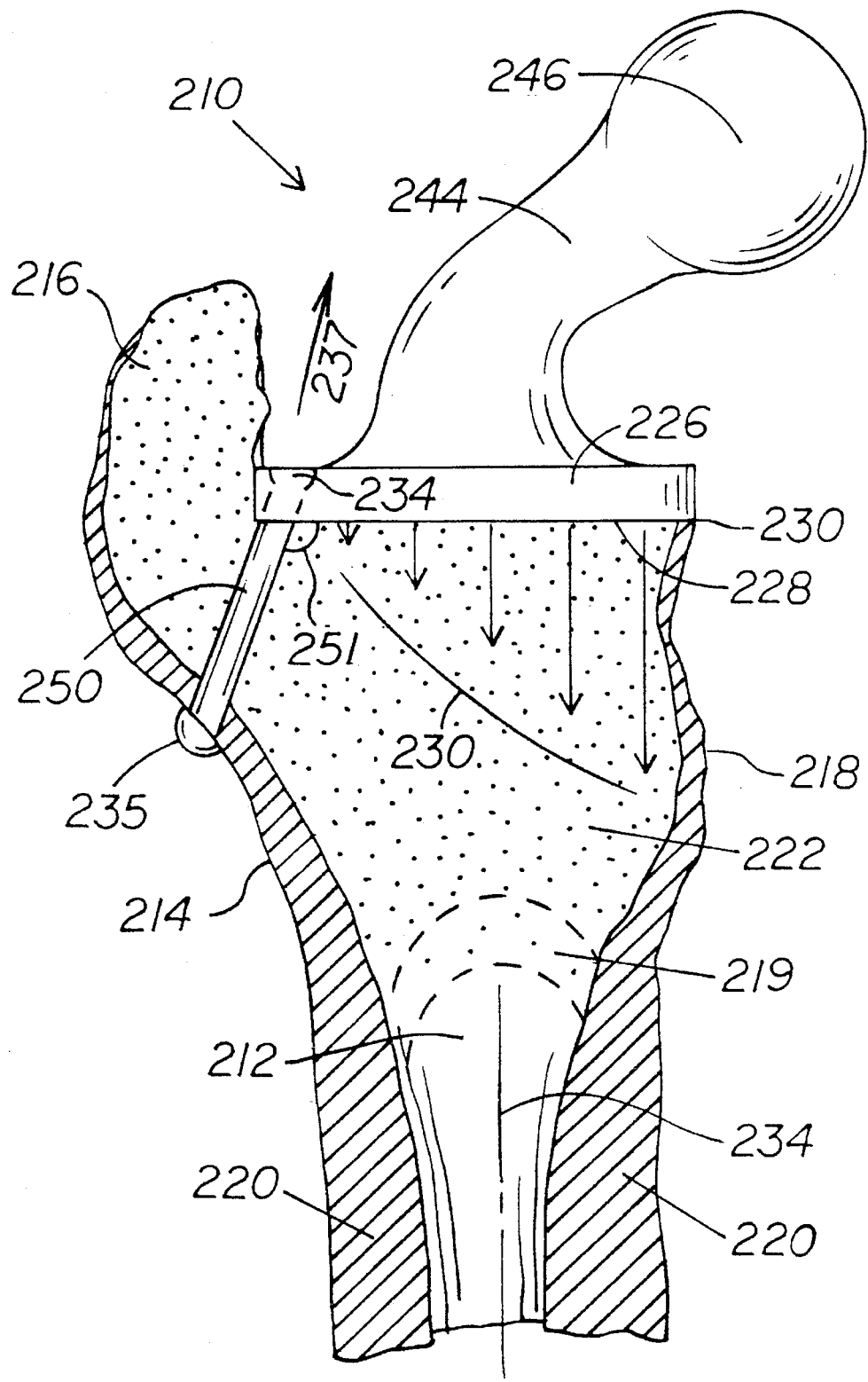
FIG. 2 is a side-view drawing of a hip system according to the invention installed on a resected femoral shaft with vectors used to indicate lift-off avoidance and force conversion.

FIG. 2 is a side-view drawing of a hip system according to the invention, indicated generally at 210, and installed on the proximal end of a femur shown in cross section. Features of the femur in the vicinity of the installation include its lateral side, 214, the greater trochanter 216, and the protrusion of the lesser trochanter at 218. A hard layer of cortical bone 220 encases soft cancellous bone 222 comprising the metaphyseal region of the bone. Below the metaphyseal region, there is a transition region 219, below which begins the medullary cavity or canal 212. The longitudinal axis of the femur is shown generally with the line 234.

The invention includes a body having a flanged portion 226 with a bottom surface 228 which seats against a surface resected on the shaft of the femur. In the preferred embodiment, these surfaces are substantially perpendicular to the longitudinal axis 234 of the femur, though non-transverse resections are also possible, as are concave and convex mating surfaces. One requirement in keeping with the invention however, is that forces applied during use be converted into compressive stress along or parallel to the femoral axis, as will be described in more detail shortly.

An elongated anchoring device 250 engages at a point on the lateral periphery of the flanged portion 226, extends downward and through a passage formed through the femoral shaft in an area below the greater trochanter 216, and anchors at a point 235 against the lateral cortex 214. This anchoring device 250 will herein be referred to as anchoring rod, though the device may comprise a rod, a tube, or any combination thereof. The upper portion of the flanged body in this embodiment assumes a bent neck shape 244 which terminates in a ball-shaped head end 246. Without this anchoring mechanism, should a downward torque be applied to the ball-shaped head end 246, tensile and compressive forces will be generated on either side of the body, resulting in an immediate lift-off hazard, as shown by arrow 237. However, with the addition of the anchoring rod 250, the same downward torque now produces only compressive forces 230, as the body is now forced to pivot about the point 234 where the anchoring rod is secured to the flange. Note that if an alternative body including an integral anchoring rod is instead utilized, the pivot point will be moved from the vicinity of point 234 to a point in the vicinity of 235, assuming there is no "play" between the rod 250 and the body itself.

The upper end of the rod where it engages with flange 226 is preferably made larger than the diameter of the rod itself so that it may be inserted downwardly to the lateral side of the femur yet not be pulled entirely through the flange itself. In the preferred embodiment, this upper end of the rod is hemispherical in shape, with the opening associated with the flange being cup-shaped to receive the hemispherical end of the rod, thereby facilitating a slight degree of freedom between the rod and body proper. It should be pointed out that the rod may be secured at various points along the lateral periphery of the flange, and that the angle 251 formed between the anchoring rod and the bottom surface 228 need not be limited to that measurable from FIG. 2.

Figure 3:
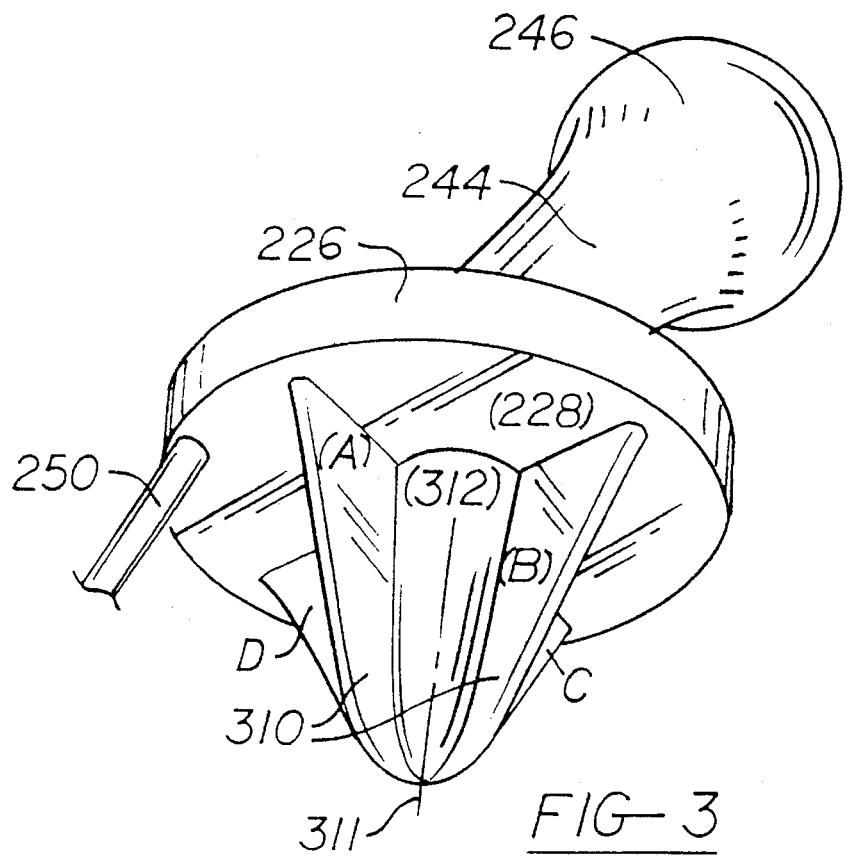
FIG. 3 is an oblique drawing of the invention illustrating one form of anti-rotation means, in this case a plurality of fins, which may be added to further limit movement of the implant with respect to the femur.

Now turning to FIG. 3, there is shown a bottom view of the invention from an oblique perspective, showing a preferred anti-rotation means in the form of one or more fins 310 which extend radially outward from a line 311 more or less central to the bottom surface 228 and transverse with respect thereto. These fins 310 preferably extend outwardly from a central bullet-like feature 312 which helps to facilitate installation and which, in one embodiment, further serves as the outer portion of a receptacle having a self-holding taper into which a separate head/neck component may be installed, as will be described with reference to FIGS. 4 and 5. These fins 310 engage with grooves formed in the bone upon implantation, thereby limiting the rotational motion of the system relative to the femur. While four fins are illustrated, a greater or lesser number may be used, and other arrangements, including curved fins, posts, and so forth, may alternatively be employed, or used in conjunction with a number of other bone-engaging orthopedic devices to prevent rotation. The four fins evident in FIG. 3 are labeled A through D so as to identify them in subsequent drawings. Note that from this perspective, the flange 226 of the body appears as a plate from which the anti-rotation means, in this case, fins, extend.

Figure 4:
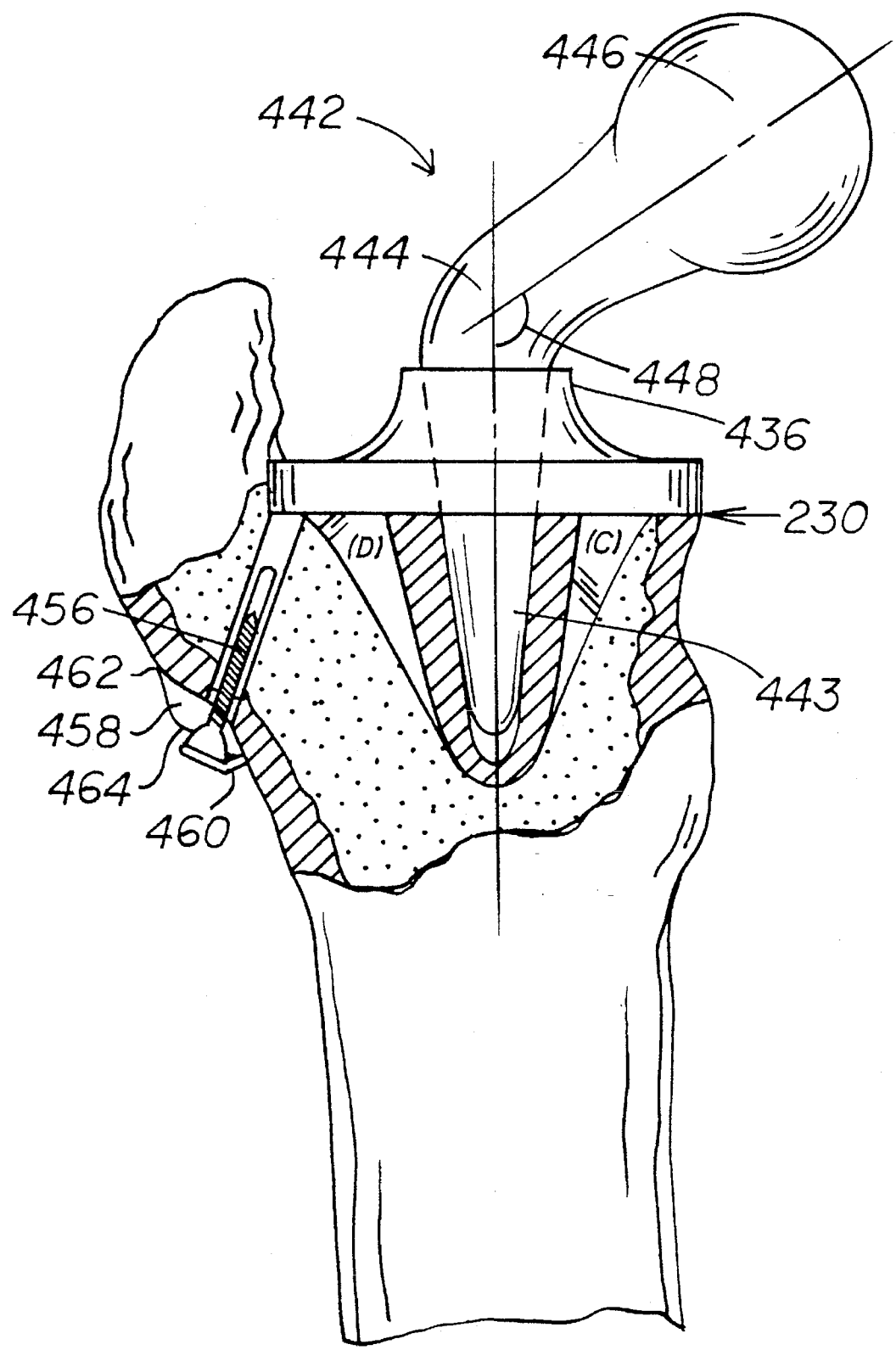
FIG. 4 is a side-view drawing in partial cross-section of an embodiment of the invention utilizing a self-holding taper between the flanged body and a head/neck component.

FIG. 4 is a side view drawing of a preferred embodiment of the invention making use of a separate head/neck component shown generally at 442. The body of the prosthesis, including the anti-rotation fins introduced in regard to FIG. 3, is shown in cross-section below the cut line 230, and certain portions of the bone have been removed to reveal details. The head/neck component, however, is shown as a solid unit. In this embodiment, the body of the implant includes a tapered, conically shaped cavity defining a receptacle into which a stem end 443 of the separate head/neck component is force-fit. In addition to its tapered stem 443, the head/neck component includes an integrally formed neck portion 444 which terminates into a ball-shaped head end 446 adapted to be received by the acetabulum of the patient after installation. The neck 444 is bent at an obtuse angle 448 with respect to the line 311 of FIG. 3. A number of head/neck assemblies formed substantially in accordance with the present invention may thus be made available, with the orthopedic surgeon selecting among them for one having an angle, ball size and neck length most suitably matched to the physical characteristics of the patient.

Figure 5:
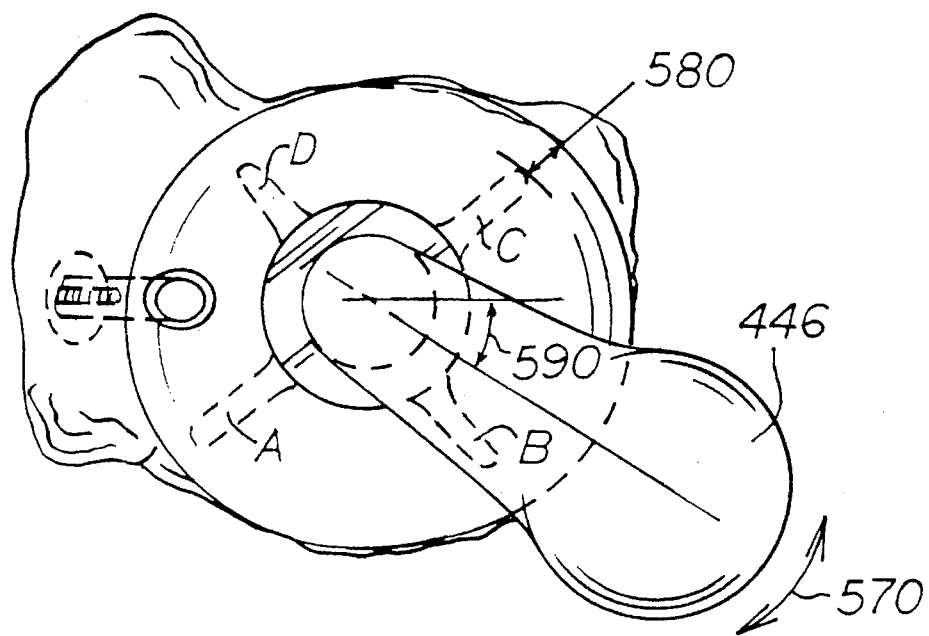
FIG. 5 is a top-view drawing of the hip system embodiment of FIG. 4, indicating where the anchoring rod is secured to the rim of the flanged, and how the head/neck assembly may be selected and rotated to meet geometric requirements prior to establishing a unitary structure.

In the illustrated embodiment of FIGS. 4 and 5, the taper of the stem 443 of the head/neck component includes a self-holding taper, preferably of the Morse type. Such self-holding tapers are known in the mechanical arts to include tapers which, when seated in a corresponding socket, form a stable, unitary structure due to the metal-to-metal joint developed therebetween. Self-holding tapers are generally fairly small, i.e., on the order of 2–5 degrees, and are to be distinguished from self-releasing tapers. There are several standard self-holding tapers known in the art beside the Morse, including Browne and Sharpe, Jarno and the American National standard tapers. A discussion of these self-holding tapers may be found in standard mechanical design texts, as, for example, in *Machinery's Handbook* 23rd Revised Edition, Oberg et al, Industrial Press, 1988 pp. 897–901, which is incorporated herein by reference.

Many recently introduced hip prostheses include a self-holding taper associated with a socket formed in a separate ball portion, and this is often generically referred to as a "Morse taper" arrangement. In FIGS. 4 and 5, however, the socket is instead formed on the femur-engaging portion of the implant, resulting in an arrangement which may be termed a "reverse" Morse taper. As will be described herein below, the present invention may be practiced with either or both self-holding taper configurations. Furthermore, it is to be understood that the present invention is not limited to any particular configuration of taper, but may include grooves, ridges, fixation members and the like to prevent relative motion once driven home.

FIG. 4 also reveals additional details associated with the preferred embodiment of the anchoring mechanism of the invention. One preferred combination of componentry includes a rod at least partially threaded to receive a compression screw 456, a washer/spacer 458, and an optional anti-back-out clip 460. Spacer 458 may be customized for each patient, having a surface 462 formed to agree with the lateral cortex of the femur, and an outer surface 464 preferably perpendicular to the axis of screw 456. In the event the anchoring rod is formed as an integral appendage to the body of the implant, a trial body with a proximal drill guide would be used to permit accurate drilling of the lateral cortex and subsequent seating of the unit. The end of the rod away from the main body would still be held against the lateral cortex with a fastener such as a compression screw and washer. As such, compression forces are transmitted to the femoral shaft in this embodiment as well.

The hip system of FIG. 4 is shown from above in FIG. 5 with the stem end 443 of the head/neck component fitted into the tapered aperture of the body. Before being finally seated into the receptacle, the head/neck component may be pivoted, as indicated with two-headed arrow 570, in order to assume a preferred geometry, prior to final connection. Various aspects of the invention are also better seen from this perspective. Note that the shape of the flange of the body need not be of a specific geometry, but may be circular, oval shaped, or irregular, depending upon patient physiology, to enhance contact between the bottom surface of the flange and the resection made on the proximal end of the femoral shaft. Note also that the fins preferably do not extend radially outwardly to the fullest extent of the outer edge of the flange, but instead, preferably stop short a distance indicated with numerical reference 580. This is to ensure that, when urging the implant into place, the fins remain within the softer cancellous bone, and do not invade the cortex, which might crack under the forces associated with installation. Note also that the angle 590 formed between the axis of the head/neck component between the bend in the neck and the ball end 446 and that within a plane parallel to the direction of the anchoring rod, need not be an exacting angle so long as the angle is acute. Although the greatest possible conversion of externally applied force may result in compressive stress when these axes are co-linear, they need not be in order to gain the force-conversion advantage of this invention. As a final reference to FIG. 5, note that although the upper end of the anchoring rod attaches to the flanged portion of the body more or less between two of the anti-rotation fins, this is not a requirement either, as the fins may be located in positions other than those shown, and, in alternative constructions, the upper end of the anchoring rod may attach very near to or, indeed, through, a fin structure.

Figure 6:
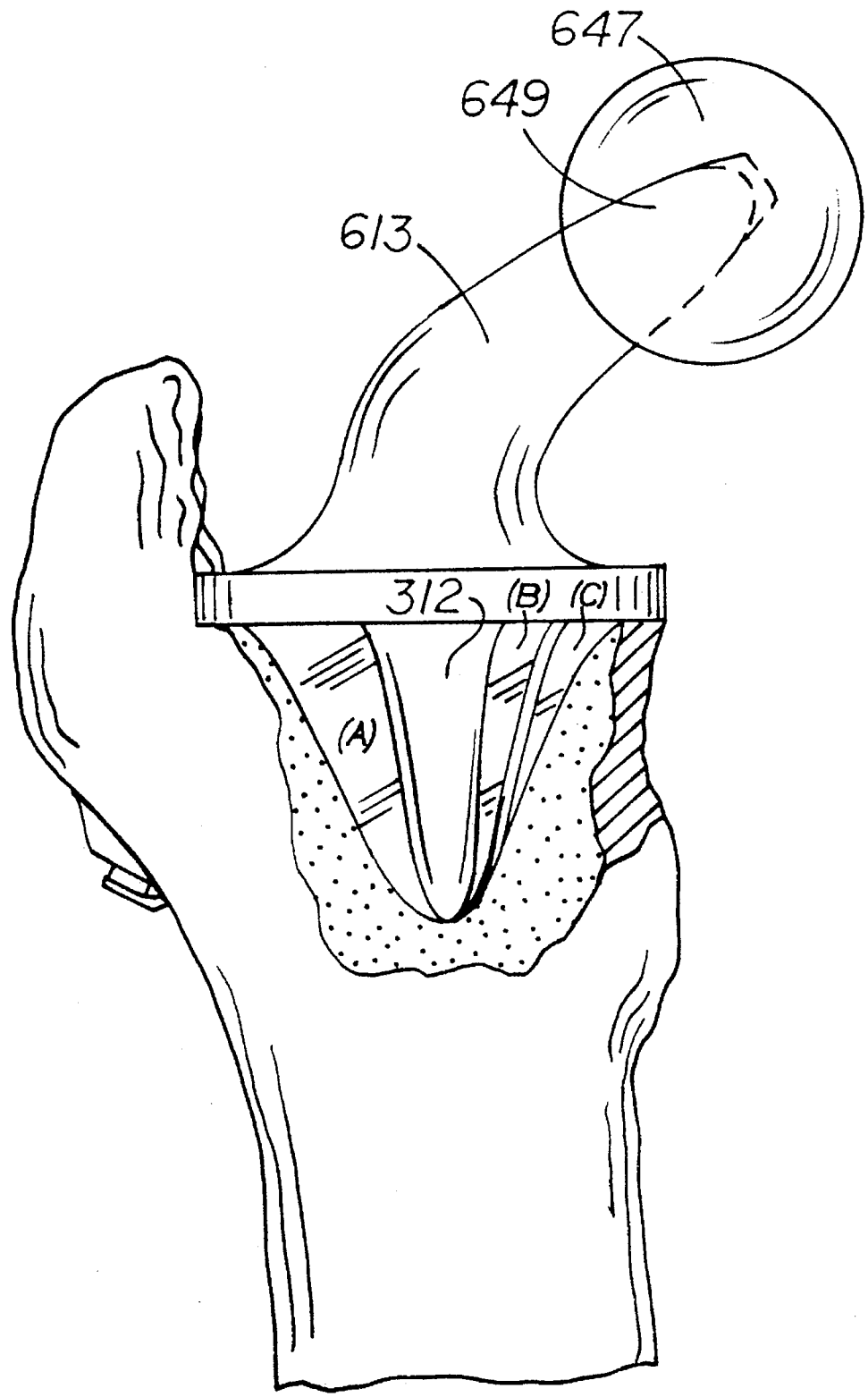
FIG. 6 is a side-view drawing in partial cross-section depicting an alternative embodiment of the invention, wherein the neck is integrally formed with the flanged body, but wherein a separate ball component attaches to an exposed neck stem using a self-holding taper.

As shown in FIG. 6, the present invention is not limited to a reverse-Morse taper but may use a standard Morse taper; that is, with a ball component 647 including a tapered receptacle, and with the neck 643 integrally formed and extending upwardly from the upper portion of the flanged body and providing a tapered stem 649. In FIG. 6, although a portion of the bone is cut away to reveal the implant, the implant itself, including anti-rotation fins, is shown in solid form. As such, using the fin configuration depicted in FIGS. 3 and 5, three of the fins, (A), (B) and (C), are evident in the figure.

Installation of the present hip system may proceed in accordance with the following preferred method. First, any of the standard approaches to the hip may be utilized, such as those described in Hoppenfield, *Campbell's Operative Orthopaedics*. The hip is dislocated, also using standard procedures, then a transverse or horizontal femoral neck osteotomy is made proximal to the lesser trochanter at a distance determined by preoperative planning as optimal for a given patient. Having performed this cut, a reamer is used to smooth out irregularities of the cut surface if necessary.

A template is used to determine the optimal size of the implant and this step may be performed preoperatively using radiology or computer-aided tomography. A central hole is formed in the bone to receive a conical bone tap and slots for a punch are used to prepare the bone for acceptance of the de-rotation fins of the implant. The implant body is seated into place, with or without cement, and with or without having a surface conductive to bone ingrowth. The present invention is not precluded from taking advantage of any current ingrowth techniques, including the use of plasma-spray-roughening, titanium mesh, and porous-coated beads, and may further include hydroxy-apatite treatment of any of the above.

A drill is used to perforate the lateral cortex, with the bit entering through the lateral chute formed in the rim of the body. A depth gauge is used to determine the length of the lateral anchoring rod, and the appropriate shaped washer is selected depending upon the curvature of the lateral cortex. The anchoring rod is secured to the washer laterally by means of a compression-type fastener.

Trial head/neck or ball components are used with the options of different head diameters, neck length and offset angles. Rotation may be determined and marked with a marking pen so that the real implant will be in the optimal position when forced into place. After installation of the actual head/neck or ball components, the hip is reduced in accordance with standard procedures and closure is performed.

Thus, in one embodiment the hip system of the present invention provides a separate head/neck assembly with reverse-Morse taper to allow changing of neck length, offset and rotation after fixation of the housing component. A standard Morse tapering may alternatively be utilized, with the neck portion being integrally formed with a flanged body. A lateral anchoring rod converts tensile forces, which would otherwise be lateral to the midline of the prosthesis, into compressive forces under the body of the implant. This prevents lift-off laterally and the resulting compressive forces are highly preferably for the stability either bone ingrowth or bone cement-interfaces. Anti-rotation means counteract the large posteriorly directed forces of the proximal femur to prevent retrovision of the implanted housing. These features, working in combination, conserve bone material of both the femur and the acetabular area to which the ball/head cooperates, thereby providing a host bed to permit primary hip arthroplasty, which is particularly important to the younger patient.

Having thus described my invention, I claim:

1. A bone-conserving prothesis adapted for installation on the shaft of a femur at its proximal end, comprising:
   a flanged body having an upper portion and a bottom surface adapted to mate against and apply compressive force to a surface resected on the proximal end of a femur;
   an elongated member extending downwardly and adapted to extend through the shaft of the femur, the member having a first end secured at a point proximate to the periphery of the flanged body, and a second end for anchoring to the lateral cortex of the femur, thus establishing a pivot point where the member is secured to the body to prevent lift-off of the body and to direct the compressive force along the longitudinal axis of the femur;
   a neck component bent at an obtuse angle and having first and second ends, the first end being connected to the body and extending upwardly therefrom; and
   a head component connected to the neck component second end, at least a portion of the outer surface of the head component being hemispherical for acetabular engagement,
   whereby forces applied to the head component during use are converted into the compressive force through the interface between the bottom surface of the flanged body and the resected surface on the femur.

2. The prosthesis of claim 1 wherein the neck component is connected to the body by means of a self-holding taper.

3. The prosthesis of claim 2 wherein the self-holding taper is of the Morse type.

4. The prosthesis of claim 1 wherein the head component is connected to the second end of the neck component by means of a self-holding taper.

5. The prosthesis of claim 4 wherein the self-holding taper is of the Morse type.

6. The prosthesis of claim 1 wherein the bottom surface of flanged body is substantially perpendicular to the axis of the femur.

7. The prosthesis of claim 1 further including anti-rotation means extending downwardly from the bottom surface of the flanged body to reduce rotation of the body relative to said femur.

8. The prosthesis of claim 7, the anti-rotation means including a plurality of fins extending downwardly from the bottom surface of the flanged body and extending radially outwardly from a line perpendicular to the bottom surface.

9. The prosthesis of claim 1, wherein the second end of the rod is anchored to the lateral cortex by means of a compression-type fastener.

10. The prosthesis of claim 9, further including means to prevent the fastener from backing out.

11. A bone-conserving prosthesis for a femur having a shaft with a longitudinal axis and a lateral side, comprising:
    a body having an upper surface and a planar lower surface, the lower surface being adapted for fixation to a flat resection on the proximal end of a femur, the upper surface transitioning to a bent neck shape, the end of the neck including a spherically shaped head end adapted for operative engagement with the acetabulum of the hip; and
    an anchoring rod having a first end secured along the lateral periphery of the body acting as a hinge upon installation, the rod being adapted to extend through a channel bored through the shaft of the femur, the rod having a second end configured to be secured along the outer lateral cortex of the femur, the body so hinged causing the planar lower surface of the base unit to be urged against the flat resection of the femur as forces are applied to the spherically-shaped head end during use, at least a portion of the applied forces being converted into compressive forces parallel to the axis of the femur.

12. The prosthesis of claim 11, wherein the resection is substantially perpendicular to the axis of the femur and the planar lower surface is adapted to mate with the resection.

13. The prosthesis of claim 11 wherein the bent neck includes an integrally formed spherically shaped head end, the other end of the neck having a tapered stem, and wherein the flanged body includes a receptacle configured to receive the stem.

14. The prosthesis of claim 11 wherein said neck is integrally formed with the body and includes a tapered stem end, and including a separate spherically shaped head component with a receptacle configured to receive the tapered stem end of the neck.

15. The prosthesis of claim 11 wherein the lower surface includes one or more protrusions configured for implantation into the metaphysical region of the femur to reduce rotation of the body relative to the femur.

16. In an extramedullary head/neck prosthesis of the type including a thrust plate urged against a surface formed on the proximal end of the femoral shaft and a rod adapted to extend through the shaft of the femur to its lateral side, the improvement comprising:
    a body including an integrally formed thrust plate adapted to be substantially perpendicular to the longitudinal axis of the femoral shaft upon installation; and
    a rod having a first end secured near the lateral periphery of said plate upon installation, the rod being adapted to extend through the femoral shaft to a second end secured on the lateral side of the femur, the combination of the plate and rod being operative to convert forces exerted upon the head during use of the prosthesis into compressive stress directed substantially along the longitudinal axis of the femur, the point where the first end is secured to the lateral periphery of the plate acting as a hinge to assist in the conversion of the forces.

17. The prosthesis of claim 1, wherein the bottom surface of the flanged body is substantially planar.

* * * * *